United States Patent [19]

Durette

[11] Patent Number: 5,918,600
[45] Date of Patent: Jul. 6, 1999

[54] OCULAR SHIELD AGAINST SURGICAL LASER ENERGY

[76] Inventor: Jean-Francois Durette, 1170 East, Henri-Bourassa Blvd., Montreal, Quebec, Canada

[21] Appl. No.: 08/863,214

[22] Filed: May 27, 1997

[51] Int. Cl.⁶ ......................................................... A61F 11/00
[52] U.S. Cl. .................................. 128/857; 128/858; 2/15
[58] Field of Search ..................... 128/846, 857, 128/858; 2/9, 12, 15

[56] References Cited

U.S. PATENT DOCUMENTS

| | | | |
|---|---|---|---|
| 1,275,127 | 8/1918 | Campbell | 2/15 |
| 1,528,282 | 3/1925 | White | 2/12 |
| 2,283,752 | 5/1942 | Gonsett | 2/15 |
| 4,162,542 | 7/1979 | Frank | 2/15 |
| 4,331,136 | 5/1982 | Russell et al. . | |
| 4,719,909 | 1/1988 | Micchia et al. . | |
| 5,151,095 | 9/1992 | Teeple | 128/849 |

FOREIGN PATENT DOCUMENTS

WO 86/02262   4/1986   WIPO .

*Primary Examiner*—Michael A. Brown
*Attorney, Agent, or Firm*—James C. Nemmers

[57] ABSTRACT

An external ocular protective device that has eye shields of non-reflective stainless steel or titanium joined together by an adjustable spring-type nose piece and held tightly over the patient's eyes by use of an adjustable elastic band placed around and behind the patient's head. The members that connect the eye shields and also provide for holding the shields in place around the patient's head are preferably very thin flexible wires that extend away from the patient's head to allow the surgeon to work any of the areas of the face without interference.

6 Claims, 2 Drawing Sheets

OCULAR SHIELD AGAINST SURGICAL LASER ENERGY

BACKGROUND OF THE INVENTION

Lasers are being used with increasing frequency in a variety of surgical procedures. Use of laser devices for surgical procedures has many advantages but also some risks. In order to minimize risk to the patient, especially when procedures are being performed on the face or head, ocular shields have been used to protect the patient's eye so as to diffuse laser energy that might have been aimed inadvertently at the patient's eyes or globe and which could cause damage if unprotected. Protection of the patient's eyes is especially critical when lasers are used for skin resurfacing or incisional procedures performed on the head and neck of the patient.

At the present time, there are known and used ocular shields that are designed to conform to the ocular globe with a vault over the cornea. These shields are inserted behind the lids over the patient's eyes usually after application of a topical anesthetic and an ophthalmic ointment to aid in the comfort and safety of the patient These shields that are inserted behind the lids over the eye must be the proper size so as to cover the entire globe. Although the smaller shields are easier to insert and remove, it is important that the entire globe be covered especially during periorbital surgery.

Because of the possibility of discomfort and necessity of inserting shields of this type to protect the eyes, surgeons sometimes use either plastic suntan goggles or simply wet gauze placed over the eyes when not working really near the ocular globe. However, when the procedure is closer to the eye, the ocular shields must be inserted beneath the lids in order to provide adequate protection.

There is therefore a need for improved external ocular shields that are safe by covering the entire globe and lids and are comfortable for the patient and practical for the surgeon to use. Any such ocular shields must be autoclavable and totally non-reflective to the laser beam so as to prevent the laser beam from passing through and reflecting back onto the surgeon or other personnel in the operating room.

SUMMARY OF THE INVENTION

The invention provides external ocular protective shields that have non-reflective stainless steel shields joined together by an adjustable spring-tape nose piece and held tightly over the patient's eyes and lids by use of an elastic band placed around and behind the patient's head. The bands are removable for separate sterilization. The members that connect the eye shields and also provide for holding the shields in place around the patient's head are preferably very thin flexible wires that extend away from the patient's head to allow the surgeon to work any of the areas of the face without interference from the shields.

DESCRIPTION OF THE PREFERRED EMBODIMENT OF THE INVENTION

Figure 1:
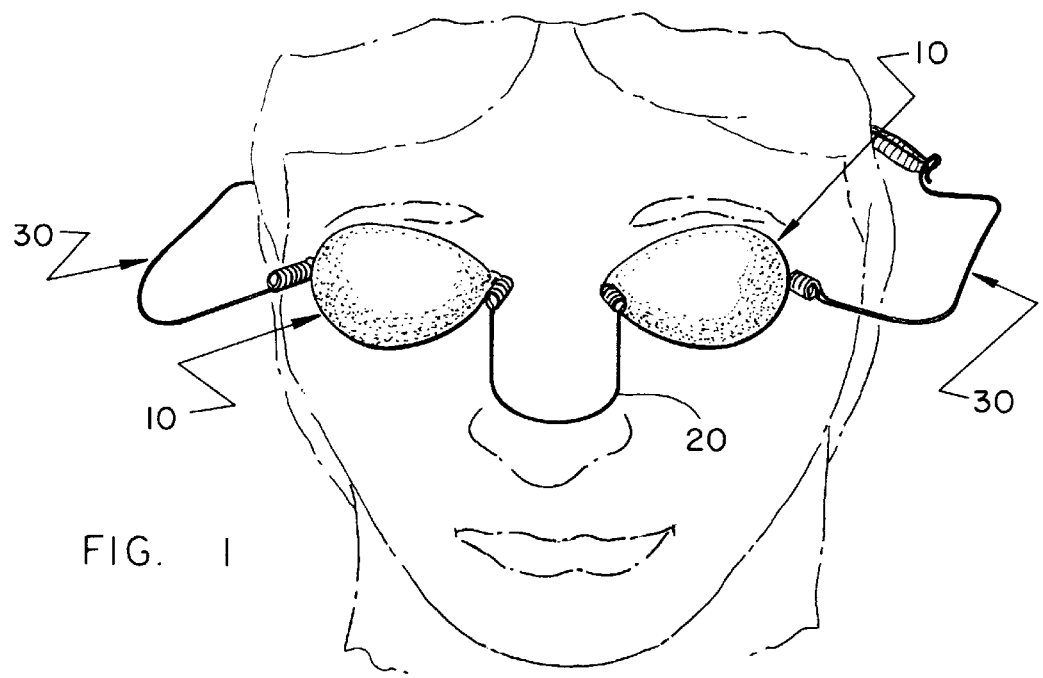
FIG. 1 is a front view showing ocular shields in place covering the eyes of the patient.
Figure 4:
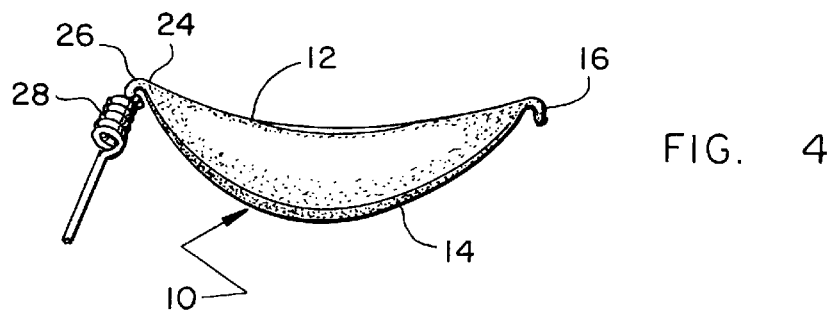
FIG. 4 is a view of one of the shields with the nose wire removed to show the connecting hook.
Figure 2:
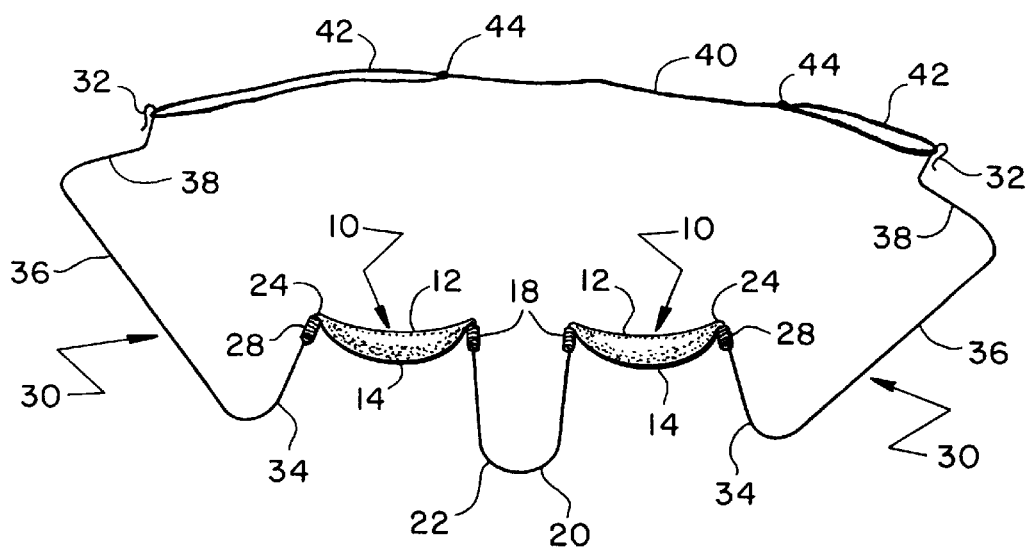
FIG. 2 is a top view of the shield illustrating the connecting and holding components.
Figure 3:
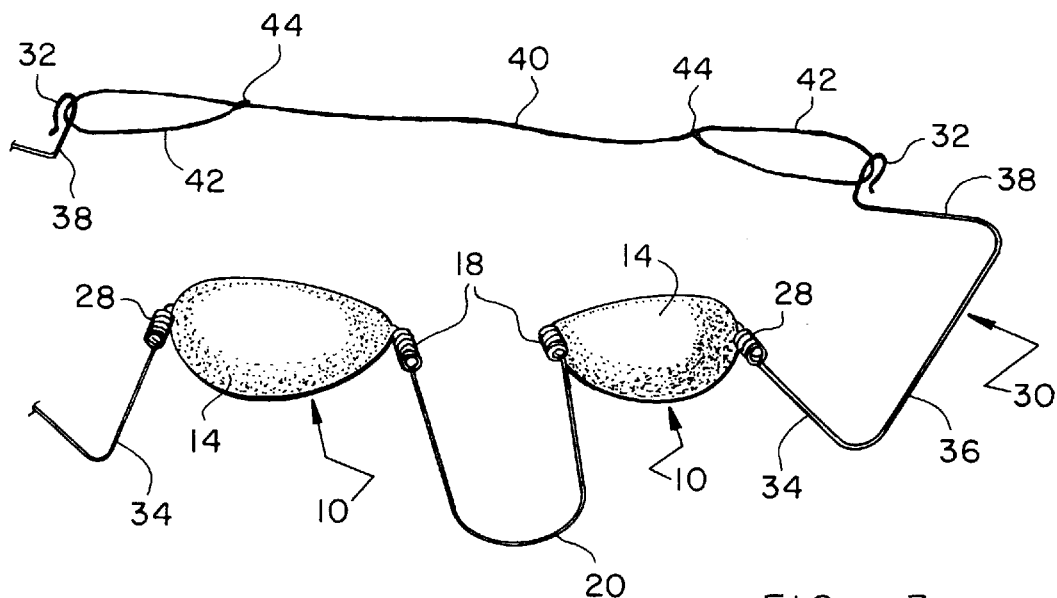
FIG. 3 is a perspective view further illustrating the relationship of the shields, the connecting wires and elastic bands.

Referring first to FIGS. 1, 2, 3 and 4, the device of the invention includes a separate shield 10 for each of the eyes. Each shield is sized and shaped to cover the entire eye socket beneath the eyebrow and above the cheekbone and extending between the bridge of the nose and the temple. Each shield 10 has an inner surface 12 shaped to comfortably fit over the ocular globe and eye lid and a curved outer surface 14. The shields 10 are constructed of material, preferably metal such as stainless steel, titanium, etc. that has been surface treated so as to be non-reflective. The shields 10 are approximately 1 mm. in thickness. The material of the shields 10 will block the laser beam from passing through the shields 10. The outer surface 14 of each shield 10 is totally non-reflective to laser energy so as not to allow the laser energy to be reflected from the shield 10 to the surgeon or other personnel in the operating room. Surface treatments are well known to those skilled in the art to make the outer surface 12 of each shield 10 sufficiently non-reflective to diffuse the laser energy.

The inner corners of the shields 10 that rest near the nose of the patient are provided with an outwardly curved hook 16 (see FIG. 4) to which there is attached the coiled end 18 of a spring wire nose piece 20. The nose piece 20 biases the inner corners of the shields 10 toward each other, but the resiliency of the material in the nose piece 20 allows the shields 10 to be adjustably fit to the facial anatomy of the patient wearing the protective device. Also, the nose piece 20 extends generally outwardly from the shields 10 so as to provide adequate space beneath and around the nose piece 20 for the surgeon to perform any surgical procedures without interference from the nose piece 20. The nose piece 20 can be curved at its outer end 22 as shown in the drawings or the outer end 22 may be straight.

To comfortably hold the shields 10 in place on the patient and also provide a tight fit over the ocular globes and lids, the outer corners 24 of the shields 10 are also provided with attachment hooks 26 which curve outwardly away from the shields 10. These hooks provide for attachment of the coiled ends 28 of the temple wires 30, each of which wires 30 terminates in a free end with a retaining hook 32. Each of the temple wires 30 has a first portion 34 that extends outwardly away from the shield 10 and a second portion 36 which extends rearwardly toward the ear of the patient when the device is being worn. As best seen in FIG. 1, both the first portion 34 and second portion 36 are a considerable distance away from the head of the patient so as not to interfere with any of the surgical procedures being performed on the patient Each of the temple wires 30 also has a third portion 38 which extends inwardly toward the patient's head with the retaining hooks 32 being formed at the terminal ends of the third portions 38. Retaining hooks 32 provide for attachment of an elastic band 40 which fits around the back of the head of the patient to hold the external ocular shield device tightly and comfortably in place. Preferably, the length of the adjustable band 40 is adjustable in any suitable way such as providing loops 42 with slideable connectors 44. The elastic band 40 is easily removable from the retaining hooks 32 so that it can be separately sterilized. Also, since the elastic band 40 can become damaged if hit by a laser beam, the elastic band 40 can be easily replaced.

The temple wires 30 are also made of a spring wire material so that when the device of the invention is in place and properly adjusted on the patient, the eye shields 10 will fit tightly and comfortably over the ocular globes and lids.

A tight and comfortable fit of the external shields 10 around the patient's eyes is necessary not only to directly block the laser beam to protect the eyes, but a proper fit will block the high energy light which can cause anxiety in the patient when the patient is not sedated. This embodiment is used primarily if the surgeon wishes to perform a procedure on the patient's skin between the eye and ear or over the nose.

Figure 5:
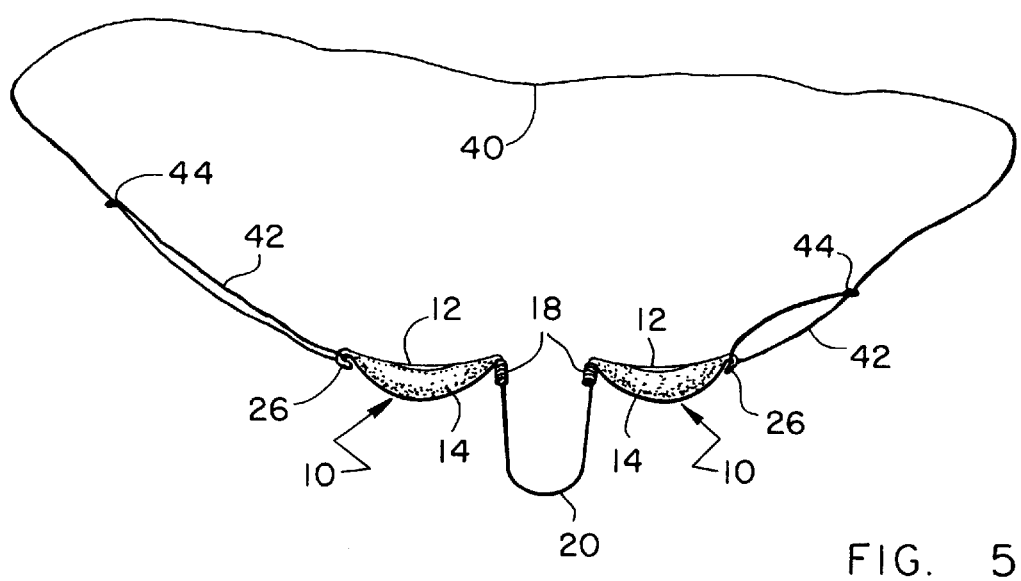
FIG. 5 is a top view of another embodiment of the invention in which the temple wires are eliminated and a single elastic band is used to hold the shields in place.

FIG. 5 shows a second embodiment of the invention in which the temple wires 30 are not used, but rather a longer elastic band 40 is used, which band 40 is connected directly to the attachment hooks 26 at the outer corners of the shields 10. These hooks 26 are bent to a nearly closed position so as to hold the band 40 securely in place while still allowing voluntary removal and insertion of the band 40. This embodiment will provide a protective device that is simpler and less expensive to produce. More importantly, no elevated wires will be in the way of the surgeon, especially when the surgeon does not have to treat the nasal or temple areas.

From the foregoing description, it will be evident to those skilled in the art that the protective device of the invention has many features and advantages over prior art devices. The shields 10 are worn externally and provide a tight and comfortable fit that assures full protection of the ocular globes and lids during any surgical procedures using lasers. The nose and temple wires and elastic band combinations provide for adjustability of the device to accommodate the anatomy of any patient The optional use of the temple wires also facilitates use of the protective device of the invention for any procedure which is to be performed near the temple where the elastic would be in the way of the surgeon. Because the elastic band can be quickly and easily removed or even discarded, the shields and connecting wires can be quickly and easily autoclaved for reuse.

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included within the scope of the following claims.

What is claimed is as follows:

1. An external protective device for protecting the eyes and the lids of a patient against surgical laser energy, said device comprising: a pair of shields each of which has an inner end and an outer end and is of sufficient size to cover an eye of the patient; each shield being made of a material that can block laser energy and having an outer surface that is non-reflective; a nose piece joining the inner ends of the shields together in spaced apart relationship so as to position the shields over the eyes of the patient; a temple wire connected to the outer end of each of the shields, the temple wires extending outwardly from the head of the patient and then rearwardly; an elastic member connected to the temple wires and adapted to be placed around and behind the patient's head to hold the shields over the patient's eyes; the nose piece and the temple wires being of very thin flexible wires that extend away from the patient's head a sufficient distance to allow a surgeon to work on any of the areas of the patient's head without interference; and the nose piece and temple wires each being connected to the shields by coiled springs, the springs providing for adjustability of the nose piece and temple wires to adapt the device to fit any patient.

2. The protective device of claim 1 in which the elastic member is adjustable and removable from the device for separate sterilization.

3. The protective device of claim 2 in which the shields are made of stainless steel or titanium.

4. An external protective device for protecting the eyes and the lids of a patient against surgical laser energy, said device comprising: a pair of shields each of which has an inner end and an outer end and is of sufficient size to cover an eye of the patient; each shield being made of a material that can block laser energy and having an outer surface that is non-reflective; a nose piece joining the inner ends of the shields together in spaced apart relationship so as to position the shields over the eyes of the patient; the nose piece being of a very thin flexible wire connected to the shields by coiled springs, the springs providing for adjustability of the nose piece to adapt the device to fit any patient, the nose piece extending outwardly from the nose of the patient a sufficient distance so as to create a space between the nose piece and the nose to allow a surgeon to work on the patient's nose without interference from the nose piece; and an elastic member connected to the shields and adapted to be placed around and behind the patient's head to hold the shields over the patient's eyes.

5. The protective device of claim 4 in which the elastic member is adjustable and removable from the device for separate sterilization.

6. The protective device of claim 5 in which the shields are made of stainless steel or titanium.

* * * * *